US005607979A

United States Patent [19]
McCreery

[11] Patent Number: 5,607,979
[45] Date of Patent: Mar. 4, 1997

[54] TOPICAL SKIN PROTECTANTS

[75] Inventor: Michael J. McCreery, Xenia, Ohio

[73] Assignee: The United States of America as represented by the Secretary of the Army, Washington, D.C.

[21] Appl. No.: 453,715

[22] Filed: May 30, 1995

[51] Int. Cl.$^6$ .............. A61K 31/02; A61K 31/08
[52] U.S. Cl. .......... 514/759; 514/723; 514/772; 514/789; 514/844; 514/937; 514/939; 514/944; 514/947; 514/845; 514/846; 514/847; 514/873
[58] Field of Search .................. 514/723, 759, 514/772, 789, 844, 845, 846, 847, 873, 932, 947, 944

[56] References Cited

U.S. PATENT DOCUMENTS 4,751,075  6/1988  Chernowsky et al. ............ 514/969
4,803,067  2/1989  Drunetta et al. .................... 424/63
5,019,604  5/1991  Lemole ............................. 514/969

OTHER PUBLICATIONS

McCreery et al, "Formulation Optimization for Perflrorronated Topical Skin Protectants" Abstract U.S. Army Medical Research and Development Command 1993 Medical Defense Bioscience Review Proceedings May 10–13, 1993 Proceedings, vol. 1, pp. 293–294.

Snider et al. "An in vitro Cultured Skin Penetration" . . . Abstract #341, 1994 Annual Meeting of the Society of Toxicology plus text of poster.

*Primary Examiner*—Shelley A. Dodson
*Attorney, Agent, or Firm*—John Francis Moran

[57] ABSTRACT

Creams formed from about 35% to about 50% fine particulates of certain poly(tetrafluoroethylene) (PTFE) resins dispersed in perfluorinated polyether oils having viscosities from about 20 cSt to about 350 cSt afford good protection against chemical warfare agents such as sulfur mustard (HD), lewisite (L), sulfur mustard/Lewisite mixtures (HL), pinacolyl methylphosphonofluoridate (soman or GD), thickened soman (TGD) and O-ethyl S-2-diisopropylaminoethyl methylphosphonothiolate (vx).

11 Claims, No Drawings

TOPICAL SKIN PROTECTANTS

BACKGROUND OF THE INVENTION

The need for topical skin protectants (TSP) to protect soldiers from the threat of dermal exposure to chemical warfare agents (CWAs) arose during World War I. During World War II several nations developed and distributed TSPs, in the United States, M-5 ointment, a petroleum-based oil containing chloramine B, which reacts with and neutralizes sulfur mustard. Although M-5 is efficacious, its oily consistency makes it difficult to keep it in place and its user acceptability has not been good. In addition, extended use of M-5 has caused a high incidence of skin irritation.

TSPs require an inert material which can be applied on the skin in a thin layer to form an antipenetrant barrier to all known CWAs or other contact irritants and will not interfere excessively with normal skin functions. Improved TSPs are needed for protecting military personnel and civilians from percutaneous exposure to CWAs and protecting the skin from contact dermatitis arising from other sources as well.

A preferred TSP affords protection against CWAs and other toxic or irritating materials in all of the forms in which they might be encountered-liquid, aerosolized liquid and vapor. For example, perhaps the best-known vesicant CWA is 2,2'-dichlorodiethylsulfide (also known as "HD" or "sulfur mustard"), which was first used during World War I and is believed to have been used in during the recent Afghan and Iran/Iraq conflicts. It appears that only a small minority (about 1%) of the injuries caused by HD have been the result of direct liquid contact and only about 22% by indirect contact with liquid. The remainder of casualties has been attributed to HD vapor and/or aerosolized liquid.

In recent years a polyethylene glycol, PEG 540, has been considered for use as a TSP by the United States Army. PEG 540 is a proprietary blend of polyethylene glycol having a nominal molecular weight of 400 with a polyethylene glycol having a nominal molecular weight of 1450 to form a mixture of nominal 540 average molecular weight. PEG 540 is opaque to white in color and has the consistency of a soft waxy salve. PEG 540 has been used by the U.S. Army as a standard for screening the performance of candidate TSPs.

The Canadian military has developed barrier creams for use as TSPs. One product, hereinafter referred to as "Canadian Protective Cream", contains the strong nucleophile potassium 2,3-butanedione monoximate as an agent-degrading ingredient in a 1:1 mixture of polyethylene glycol monomethyl ethers MPEG 550 and MPEG 1900. Another preparation, hereinafter referred to as "Canadian Skin Cleanser", contains the same active ingredient in MPEG 550.

A variety of products have been offered commercially in civilian markets for use as protectant barriers. Among these are Barrier Biocream (Biomedic, Busnago, Italy) and Mane Street Barrier Creme (Mane Street Products Minneapolis, Minn.) both of which contain small amounts of a perfluorinated polyether; Biocontrol (Biocontrol, Coon Rapids, Minn.), which contains a modified-cellulose-based polymer; Multi Shield Skin Cream (Interpro, Haverhill, Mass.), which contains TEA-stearate in a mixture of monoethanolamine stearic acid amide, ethoxydiglycol, diethylene glycol monoethyl ether and acetic acid in water; pr88 Wash-off Hand Protection Cream (Ursula Rath GmbH, Senden, Germany), which contains glycerine in an aqueous mixture of sodium silicate, soap, emulsifier, wax and fragrance; pr99 Skin Protection Lotion (Ursula Rath), which contains PEG 300 glyceryl oleate in an aqueous mixture of cetearyl octanoate, microcrystalline wax, mineral oil, lanolin, dimethicone, tocopheryl acetate, glycerin, magnesium sulfate, phenoxy ethanol and fragrance; pr2000 Skin Care Lotion (Ursula Rath), which contains stearyl alcohol in a mixture of stearyth-7, stearyth-10, ceteareth-25, cetearyl octanoate, cetearyl alcohol, glyceryl stearate, mineral oil, dimethicone, tocopheryl nicotinate, bisabolol, glyceryl linoleate, glyceryl linolenate, panthenol, propylene glycol, phenoxy ethanol, carbomer, tetrahydroxypropyl ethylene diamine and fragrance; and Ivy Block (United Catalysts, Louisville, Ky.), which contains cyclomethicone, quaternium-18 bentonite and SD alcohol. Investigation of these materials has shown that they do not afford satisfactory protection against CWAs.

Recent work has shown that certain perfluorinated greases used as lubricants for extreme operating conditions show good protection against contact with organophosphates and protection against vesicants such as HD (Snider et al., "An in vitro Cultured Skin Penetration Model for Evaluating the Efficacies of Topical Skin Protectants Against Anticholinesterase Compounds", Abstract #341, 1994 Annual Meeting of the Society of Toxicology; McCreery et al., "Formulation Optimization for Perfluorinated Topical Skin Protectants (TSPs)", Abstract, U.S. Army Medical Research and Development Command 1993 Medical Defense Bioscience Review Proceedings May 10–13, 1993 Proceedings, Vol. 1, pp 293–4). The materials described in those publications are quite expensive but they have been used commercially as specialty greases because they provide good lubricity and they are chemically inert and stable at high temperatures. These greases are blends of finely divided polytetrafluoroethylene (PTFE) in perfluorinated polyether base oils. A typical commercially available grease contains about 15–30% PTFE dispersed in a perfluorinated polyether base oil having a viscosity of 800 cSt (20° C.) or more. Certain commercial greases have been found to afford protection against liquid CWAs both in vitro and in vivo. One such material was Fomblin® RT15, a mixture of 28–30% (w/w) Algoflon® L206 PTFE in Fomblin® YR oil sold by Ausimont, USA as an industrial grease. Other perfluorinated greases are sold by Du Pont under the Krytox® trade name. These include Krytox® LVP, a high vacuum grease containing about 30% by weight PTFE in Krytox® 16256 vacuum pump fluid; Krytox® 240AC, a mixture of about 13–16% VYDAX® 1000 in Krytox® 143AC perfluorinated oil; and Krytox® 340AC, a mixture of about 28% PTFE in Krytox® 143AC perfluorinated oil. These commercial materials have similar compositions and characteristics. All are simple mixtures of a perfluorinated polyether base oil having a viscosity of 800–2700 cSt (20° C.) or more thickened with fine polytetrafluoroethylene (PTFE) particulates. Although the compositions afford good TSP properties they are quite sticky, as would be expected for materials used as greases. Experience has shown that sticky topical products are not acceptable to users. Furthermore they may cause debris and foreign bodies to become lodged in the barrier as well, compromising its TSP qualities. In addition, perfluorinated polyethers are costly, which probably would be a practical limitation to their use in high concentrations or over long periods of time. In short, although they form effective protective barriers when applied to the skin, the commercial grease products are sufficiently sticky and expensive to make it problematical that they would be suitable as TSPs.

The basic repeating units of the base oils used in the commercial grease products differ somewhat, but both are almost totally perfluorinated, have multiple ether linkages in their mainly unbranched chains, and have average molecular weights in the range of 5,000 to 7,000. They are nearly inert chemically, do not freeze at −196° C. or boil at 280° C.; have relatively high viscosities (800–2700 cSt or more); have no odor or taste; have very low vapor pressures; and very low solubility in nearly all solvents.

The PTFE particulates used as thickeners in the commercial grease products are also similar. The particles are generally spherical in shape and have sizes ranging from 0.1 μ to 10 μ or more, but most have sizes in which >90% of the particles fall between 3 and 5 μ in size. Since their surfaces are corrugated with deep crevices, the particles possess a high surface area, up to about 15 $M^2/g$. The polymers are high molecular weight, averaging about 200,000. The structure and size make the polymers nearly chemically inert, except in strong acid.

Perfluorinated polyether base oils are typically synthesized by a chain reaction starting from perfluoroethylene or perfluoropropylene oxides. The reaction produces a distribution of molecular weights (MW) or polymer number (n) that is normally gaussian, but can be skewed to higher or lower MWs by reaction conditions. The crude products may be used directly but usually are fractioned by vacuum molecular distillation into "cuts", similar to those used as petroleum products. Each cut has an average boiling point and a boiling point range that define the molecular weight distribution. The viscosity, boiling point, vapor pressure, and other physical parameters of the oils vary proportionately with the chain length or polymer number. Some commercial products are produced by blending higher- and lower-viscosity (molecular weight) materials to obtain a desired viscosity.

Brunetta et al., U.S. Pat. No. 4,803,067, describes the use of minor amounts of perfluorinated polyether oils as ingredients of oil/water or water/oil emulsions used in formulating compositions stated to be useful as cosmetics, waterproof sunscreens, carriers for drugs and as protective and barrier creams. Pereira, U.S. Pat. No. 4,981,841, discloses water-in-oil emulsions stated to be useful as topical treatments for skin and hair which contain "skin benefit ingredients". Perfluorinated polyether oils are listed among the many possible materials to be included in minor amounts as "skin benefit ingredients". Pantini et al., U.S. Pat. No. 5,092,023, desribes cosmetic cleaning emulsions which contain minor amounts of perfluorinated polyethers among other ingredients. Oliver, French Patent Application 2,664,162, describes emulsions stated to be useful as barrier coatings which contain minor amounts of a perfluorinated polyether among other ingredients.

Maillat, U.S. Pat. No. 4,937,010, describes non-aqueous paint formulations which contain, inter alia, perfluorinated polyether oils which act as immiscible lubricating ingredients in the coatings. Some of the commercial coatings used Maillat's examples contain unstated amounts of polytetrafluoroethylene (PTFE) powder.

Trussler et al., UK Patent Application 2,244,601A, describes a conductive layer for circuit boards which contains a perfluorinated grease or gel such as Fomblin ZLHT.

SUMMARY OF THE INVENTION

It has been found that creams formed from about 35% to about 50% fine particulates of certain poly(tetrafluoroethylene) (PTFE) resins dispersed in perfluorinated polyether oils having viscosities from about 20 cSt to about 350 cSt afford good protection against chemical warfare agents such as sulfur mustard (HD), lewisite (L), sulfur mustard/Lewisite mixtures (HL), pinacolyl methylphosphonofluoridate (soman or GD), thickened soman (TGD) and O-ethyl S-2-diisopropylaminoethyl methylphosphonothiolate (VX). (Although perfluorinated polyether oils of higher viscosity containing high concentrations of PTFE have good efficacy, their user acceptance/cosmetic texture are unsatisfactory for use as TSPs.) Similarly the compositions are expected to be useful for protecting against the effects of other nerve gases, vesicants, and materials which cause contact dermatitis; contact allergens such as poison ivy, poison oak, and poison sumac; and solvents and the like which are irritating or noxious to the skin.

DETAILED DESCRIPTION OF THE INVENTION

The compositions of the invention are suspensions of finely divided PTFE in a perfluorinated polyether base oil. Recently it has been found that effective protection against CWAs can be obtained using compositions which contain concentrations of as little as 10–15% to about 30% PTFE in a base oil having a viscosity up to 1500 cSt or more sold as lubricants or greases (Snider et al. and McCreery et al., op. cit.). Those materials however are greasy or sticky. If a TSP formulation is too greasy or tacky the greasiness or tackiness significantly reduces manual dexterity and user acceptance. Although Fomblin® RT15 and other commercial greases can be easily spread to a thin film, the films remain tacky to the touch (and adhere particulates) for several hours. Superior results have been obtained with the compositions of the present invention which comprise from about 35% to about 50% of finely divided PTFE having a surface area below about 6 $M^2/g$ in a perfluorinated polyether base oil prepared from perfluoropropylene oxide which has a viscosity between about 20 and about 350 cSt. More preferred compositions comprise from about 40% to about 50% of finely divided PTFE having an average particle size from about 0.1μ to about 10μ and a surface area below about 4 $M^2/g$ in a perfluorinated polyether base oil having a viscosity between about 20 and about 350 cSt. The most preferred compositions comprise from about 40% to about 50% of finely divided PTFE having an average particle size below about 5 μ and a surface area below about 4 $M^2/g$ in a perfluorinated polyether base oil having a polydispersity below about 1.6 and a viscosity between about 20 and about 350 cSt.

A variety of perfluorinated polyether oils have been examined and found useful in the practice of the invention. Although their chemical structures vary somewhat in detail, having the preferred viscosity, all have been found useful for practice of the invention. Fomblin® HC- and Y-oils (Ausimont) are mixtures of linear polymers based on perfluoropropylene oxide having the following chain structure: $CF_3$—[$(OCF(CF_3)CF_2)_m$—$(OCF_2)_n$]—$OCF_3$. Krytox® oils (DuPont) are mixtures of linear polymers also based on perfluoropropylene oxide and have the chemical structure: F—[$(CF(CF_3)$—$CF_3O)$—]$_m CF_2CF_3$. Although they are much more costly, Fomblin® Z oils having the formula: $CF_3$—[$(OCF_2CF_2)_m$—$(OCF_2)_n$]—$OCF_3$, may also be useful in the practice of the invention. The indices m and n indicate the average number of repeating polymeric subunits in the oil molecules.

It has been found that the viscosity of perfluorinated polyether oils useful in the compositions of the invention is more significant than their structure. Oils useful in the practice of the invention may have a viscosity of from about 20 cSt to about 500 cSt or more. As the molecular weight of perfluorinated polyether oils decreases, their viscosities decrease. At very low viscosities, below about 20 cSt, the volatility of the oil becomes excessive, leading to unstable and/or short shelf-life products. When oils having viscosities much above 350 cSt are used the creams are invariably sticky or are difficult to spread, and it is also difficult to prepare compositions having high concentrations of PTFE. Some commercial products are produced by blending higher- and lower-viscosity (molecular weight) materials to obtain a desired mid-range viscosity. The data give some reason to believe that compositions based on oils which are single distillation "cuts" may be preferred to those based on blended oils. Some compositions based on high viscosity oils have similar efficacy as TSPs at lower PTFE loadings than for TSPs based on lower viscosity oils and TSPs based on high viscosity oils afford somewhat better protection against HD vapor than compositions having the same % PTFE based on low viscosity oils. However, compositions based on oils having viscosities much in excess of about 350 cSt are very sticky and therefore are less useful and less acceptable to users than compositions based on lower viscosity oils. Also it is difficult to obtain workable creams having concentrations of PTFE much in excess of about 35% when high viscosity oils are used. Since PTFE is much less costly than perfluorinated oils, TSPs of having a given effectiveness have lower overall cost when they are formulated with high PTFE levels. Thus, although TSPs having good barrier properties can be prepared using high viscosity oils, the compositions are too sticky for practical use and in addition are more costly. The compositions of the present invention which employ base oils having a viscosity of less than about 450 cSt are substantially dry to the touch.

Historically, polyethylene glycol having an average molecular weight of 540 (PEG 540) has been used as a standard in most in vitro and in vivo testing of TSPs. Because the products of the present invention have been found to be so much more effective than PEG 540, in the later stages of the present investigation all candidate materials were compared in every test against the performance of Fomblin® RT15, which earlier work has shown to afford significant protection, was chosen as the benchmark material. In vitor efficacy, in vivo efficacy, stability, and cosmetic texture (tackiness or greasiness) were compared.

EXPERIMENTAL

Preparations of various PTFE resins in a variety of perfluorinated polyethers were prepared and evaluated for effectiveness by the M8 paper assay, and were also evaluated for their greasiness/tackiness by inspection and observing their "feel" after application to the experimenters skin.

Fomblin ® RT15, PEG 540 and candidate materials were tested by challenge with neat HD. This assay is hereinafter referred to as the "M8 assay" or "M8 paper test" (see below). In general, the results of the M8 assay have proven very predictive of the efficacy of materials in subsequent in vivo testing.

The PTFE resins used were:

| PTFE | Particle Size (g) | Surface Area M²/g |
|---|---|---|
| Polymist ® F5 | 4 | 3 |
| Polymist ® F5A | 4 | 3 |
| Polymist ® XPH-284 | 7 | 3 |
| Algoflon ® L206 | 5–7 | 9 |

-continued

| PTFE | Particle Size (g) | Surface Area M²/g |
|---|---|---|
| Teflon ® MP1200 | 3–4.5 | 3.4 |
| Teflon ® MP1400 | 7–12 | 3.4 |
| Teflon ® MP1600 | 4–12 | 10 |

The perfluorinated polyether base oils used were:

| Base oil | Viscosity @ 20° C. | Density (g/ml) | MW |
|---|---|---|---|
| Galden ® D40 | 40 | 1.87 | 1000 |
| Fomblin ® Y25 | 250 | 1.90 | 3200 |
| Fomblin ® Y45 | 450 | 1.90 | 4100 |
| Fomblin ® YR | 1500 | 1.91 | 6600 |
| Krytox GPL ® 102 | 36 | 1.91 | all are 7 cSt oil |
| 103 | 80 | 1.92 | blended with |
| 104 | 180 | 1.93 | 1500 cSt oil to |
| 105 | 550 | 1.95 | obtain desired |
| 106 | 810 | 1.95 | viscosity |
| 107 | 1600 | 1.95 | 6000 |

To prepare mixtures a quantity of base oil was carefully weighed in a scintillation vial and the weight of PTFE needed to prepare the desired composition was calculated and weighed out on glassine weighing paper. The PTFE powder then was slowly mixed into the oil in the vial using a small glass stirring rod. Mixing was slow and deliberate at first to reduce loss of fine particulates into the air. Then a high speed, high shear Polytron Mixer (Brinkmann Instruments) with a medium head at a setting of 5 was used for not less than five minutes to complete mixing of the components. In addition two greases representative of commercially available materials used in the compositions of Hobson et al. and McCreery et al. (op. cit.) were included in the study. One was Fomblin® RT15 (Ausimont), which contains about 28% Algoflon L206 in Fomblin® YR oil; the other was a material supplied by Du Pont which contained about 14% PTFE in an oil having a viscosity of about 2700 cSt (Krytox® 16256).

M8 Paper Test

An 8 cm strip of white TimeMed® labeling tape, 0.15 mm thick, was perforated with three 2 cm diameter holes. The perforated tape was placed on a strip of M8 chemical detection paper and the resulting wells were filled with either Fomblin® RT15 standard or the candidate material. Approximately 0.1 mL material was dispensed from a 1 cc syringe (no needle) into the center of the well, spread with a small spatula into all regions of the well, and then one end of a glass microscope slide was dragged across the top of the well to make the surface smooth and flush with the top of the TimeMed® tape. The handling characteristics (fluidity/dryness, spreadability, stickiness or tackiness) were noted as indications of the probable suitability of the formulations for actual use. PEG 540 test sites were heated over a hot plate until all evidence of bubbles in the preparation was removed.

Tests consisted of 15 preparations (i.e., five pieces of M8 paper, each with three application sites) placed on a glass viewing stand with a mirror positioned below it for easy viewing of the bottom surface of the M8 paper. Each test consisted of 3 trials for the standard and 12 trials for the candidate material.

Dosing commenced one hour after test site preparation. CSM (8 μL) was applied to the center of each test site, which was immediately occluded with a 2 cm inside diameter plastic cap to reduce evaporation. The bottom surface of the M8 paper was observed continuously for color changes for one hour and thereafter every 0.5 hour for an additional 5 hours. The elapsed time for a color change from lavender to red (for HD), indicating CSM contact with the paper, was recorded as the breakthrough time. Results with the standard barriers showed that one or two breakthroughs in a series could be expected to occur in a random fashion because of incomplete coverage or accidental penetration of a barrier when initiating the challenge. Therefore it was judged that no distinctions should be made between materials having 0, 1 or 2 breakthroughs in the series of 12. The results of the M8 test screen are summarized in Table 1 beyond (see Results). Candidates selected on their performance against HD were also tested (0.1 mm thickness) against TGD in the same manner. The results are included in Table 1.

Tack/User Acceptability Test

Measurement of properties which would affect the ability to perform manual tasks and user acceptability of materials (hereinafter "tack") was estimated from the handling characteristics of candidate formulations and by independent evaluations by at least two persons of material applied to the skin. Each evaluator was blinded as to the identity of the materials and compositions being evaluated. The judgment included the ease or degree of spreadability, greasiness/stickiness to the touch of the area covered with the material, smoothness of the coating and its dryness to the touch. Ratings from 1 (extremely greasy or sticky and/or hard to spread), 2 (unacceptably greasy or sticky and/or hard to spread), 3 (slightly greasy or sticky) and 4 (excellent, a smooth easily spread coating which is dry to the touch) were made. A rating of 3 was judged to be the minimum acceptable value.

RESULTS

Preparation of Candidate TSPs: Initial Stability

After initial mixing, all formulations were visually inspected to estimate stability. Some formulations, particularly those in which a low viscosity oil and/or low PTFE concentrations were used, were immediately unstable and some using a high viscosity oil and high PTFE concentrations could not be mixed. Materials which separated upon cessation of mixing, or within 1–2 days were remixed for a longer time up to 15 minutes. If separation recurred, the formulation was not tested.

Results of In Vitro Evaluation

PEG 540 was maintained throughout as the process control in all tests and initially served as the standard as well. Subsequently candidates were contrasted with the Fomblin® RT15 standard as well. Data are presented in the following table according to the standard referenced.

Efficacy in vitro

Results from in vitro evaluation against HD and TGD using the M8 Paper Test are summarized in the table below. Fewer breakthroughs are indicative of higher antipenetrant activity. Fomblin® RT15 was designated as the standard material. When a scatter plot is made of the number of replicates with no breakthroughs as a function of the % PTFE in the mixture regardless of type of PTFE used or the base oil in which it is embedded a hyperbolic relationship can be seen. When PTFE concentration was equal to zero (base oil alone) no efficacy was demonstrated whatsoever. This relationship held true for all base oils tested. As PTFE is added to the base oil in greater amounts, efficacy increases to some maximum, the limit for this test (100% no breakthrough).

In vivo Efficacy:

A limited number of candidates selected on their good performance in the M8 test were also tested against contact with HD, VX and TGD in vivo using rabbits as the test animals. The number of tests was limited due to their expense, but the results showed clearly that good results in the in vitro M8 test were predictive of good in vivo results.

Additional in vivo tests conducted with selected candidates against HD vapor using hairless guinea pigs as the test animals showed that protection also was obtained. Better results were obtained in the test against HD vapor using compositions containing 50% PTFE in a given oil than with 45% PTFE in the same oil, and better results were obtained with higher viscosity oils than with lower viscosities.

TABLE 1

GALDEN D40

| PTFE % | F5A HD | F5A TGD | HD | * | F5 TGD | HD | L206 TGD | * | HD | XPH284 TGD | * |
|---|---|---|---|---|---|---|---|---|---|---|---|
| 10 | 7 | — | — | — | — | — | — | — | — | — | — |
| 20 | 1 | — | — | — | — | — | — | — | 0 | — | — |
| 25 | 1 | — | 0 | — | — | — | — | — | 0 | — | 2 |
| 30 | 0 | — | — | — | 0 | — | — | 2 | 0 | — | 2 |
| 35 | 1 | — | 0 | — | — | — | — | — | 0 | — | 2 |
| 40 | 0 | — | 0 | 2 | 0 | 4 | — | 4 | 0 | — | 2 |
| 45 | 0 | 0 | 0 | 4 | 0 | 4 | 0 | 4 | 0 | 0 | 2 |
| 50 | 0 | 0 | 0 | 4 | — | 2 | 6 | 2 | — | 4 | — |
| 55 | | ** | | | | | ** | | | ** | |

FOMBLIN Y45

| PTFE % | F5A HD | F5A TGD | 206 HD | 206 TACK | XPH284 HD | XPH284 TGD | TACK |
|---|---|---|---|---|---|---|---|
| 10 | 6 | — | — | — | 2 (12%) | — | — |
| 20 | 3 | — | 2 | — | 0 (18%) | — | — |
| 25 | 2 | — | 1 | — | 0 (24%) | — | — |
| 30 | 1 | — | 1 | — | 0 | — | — |
| 35 | 1 | — | 0 | — | 0 (36%) | 0 | 4 |
| 40 | 5 | — | ** | | ** | ** | |
| 45 | 0 | 0 | | 2 | | | |

FOMBLIN Y25

| PTFE % | F5A HD | F5A TGD | TACK | L206 HD | L206 TGD | XPH284 HD | XPH284 TGD | TACK |
|---|---|---|---|---|---|---|---|---|
| 10 | 6 | — | — | 3 | — | 0 | — | — |
| 20 | 4 | — | — | 1 | — | 8 | — | — |
| 25 | 3 | — | — | — | — | 0 | — | — |
| 30 | 3 | — | — | 0 | 1 | 0 | 1 | — |
| 35 | 0 | — | 3 | — | 2 | — | 2 | — |
| 40 | 3 | — | — | 0 | 0 | 0 | 0 | 3 |
| 45 | 1 | 0 | 3 | 0 | 1 | 0 | 1 | 3 |
| 50 | 2 | 0 | 4 | ** | 0 | — | 0 | 4 |

FOMBLIN YR

| PTFE % | F5A HD | F5A TACK | L206 HD | L206 TDG | TACK | 284 HD | 284 TACK |
|---|---|---|---|---|---|---|---|
| 8 | 0 | | 9 | — | — | 3 | — |
| 12 | 8 | | 2 | — | — | 2 | — |
| 18 | 0 | | 2 | — | — | 0 | — |
| 24 | 0 | | 5 | — | 1 | 0 | 2 |
| 28[1] | — | | 0.6 | 0 | — | — | — |
| 30 | 0 | | 2 | — | — | 0 | — |
| 36 | 0 | | 1 | — | — | 0 | — |
| 40 | — | | ** | ** | ** | | ** |

KRYTOX GPL102

| PTFE % | MP1200 HD | MP1200 TGD | MP1400 HD | MP1400 TGD | MP1500 HD | MP1500 TACK |
|---|---|---|---|---|---|---|
| 15 | — | — | — | — | 2 | 20 |
| 20 | — | — | — | — | 7 | 1 |
| 25 | — | — | — | — | 3 | 1 |
| 30 | — | — | — | — | 2 | — |
| 35 | — | — | 1 | — | 2 | — |
| 40 | — | — | 1 | 2 | ** | ** |
| 45 | — | — | 2 | 3 | | |
| 50 | — | — | 1 | 3 | | |

KRYTOX GPL104

| PTFE % | MF1200 HD | MF1200 TGD | MP1400 HD | MP1400 TGD | MP1600 HD | MP1600 TACK |
|---|---|---|---|---|---|---|
| 15 | — | — | — | — | 0 | — |
| 25 | — | 0 | 3 | — | 0 | 0 |
| 30 | — | 0 | 0 | — | 0 | 0 |
| 35 | — | — | 0 | — | — | — |
| 40 | — | — | 0 | — | — | — |
| 45 | — | — | 0 | 8 | — | 1 |
| 50 | | | | ** | | ** |

KRYTOX GPL106

| PTFE % | MP1200 HD | MP1200 TGD |
|---|---|---|
| 15 | — | — |
| 20 | — | — |
| 25 | — | — |
| 30 | 4 | — |
| 35 | 0 | — |
| 40 | 3 | — |
| 45 | 1 | — |
| 50 | 2 | — |
| 55 | 1 | 9 |

KRYTOX GPL103   KRYTOX GPL107

TABLE 1-continued

| PTFE % | MP1200 HD | MP1200 TACK | MP1400 HD | MP1400 TGD | MP1400 TACK | MP1600 HD | PTFE % | HD³ | MP1400 TDG⁴ | MP1400 TACK | PTFE % | MP1200 HD | MP1200 TACK |
|---|---|---|---|---|---|---|---|---|---|---|---|---|---|
| 15 | — |   | — | — |   | 7 | 9 | PASS | — |   |   |   |   |
| 20 | — | 2 | — | — |   | 2 | 18 | PASS | — |   |   |   |   |
| 25 | 9 |   | 6 | — | 1 | 2 | 24 | PASS | — |   |   |   |   |
| 30 | 5 |   | 5 | 1 | 2 | 6 | 30 | PASS | — |   |   |   |   |
| 35 | 1 |   | 4 | — | 2 | 7 | 36 | PASS | — |   |   |   |   |
| 40 | 3 |   | 4 | 1 | 2 | ** | 42 | PASS | MORE | 3 |   |   |   |
| 45 | 1 |   | 1 | — | 1 |   | 48 | PASS | MORE | 3 | 45 |   |   |
| 50 | ** |   |   | ** |   |   |   |   |   |   |   |   |   |

HD COLUMN IS # BREAKTHROUGHS/12 TESTED
FOMBLIN RT159/192, PEG 540 189/189
TGD COLUMN IS # OF BREAKTHROUGH/12 TESTED
*TACK
¹FOMBLIN RT159/192 = 0.6/12
²HIGHER CONCENTRATIONS COULD NOT BE PREPARED
³COMPARED TO PEG540
⁴COMPARED TO FOMBLIN RT15

It can be seen that creams with desirable tack (3–4) cannot be prepared using PTFE resins such as Algoflon L206 (9 m$^2$/g) and Teflon MP1600 (10 M$^2$/g) which have high particle surface areas. Resins having surface areas below about 4 M$^2$/g are necessary in order to prepare the non-sticky protective creams of the invention. Also, resins having low surface areas but large particle size such as Teflon MP1400 (7–12μ) and Polymist XPH284 (5–7μ) are difficult to formulate into the desired high solids creams. Therefore, resins having surface areas below about 4 M$^2$/g and particle sizes below about 5μ are preferred.

It also can be seen that compositions prepared with high viscosity oils such as Fomblin Y45, Fomblin YR and Krytox GPL106 and 107 (greater than about 350 cSt) do not afford creams with acceptable (3–4) tack ratings. The data also show that it is necessary to have at least 35% PTFE in a composition in order to achieve an acceptable tack rating, but concentrations of more than about 50% do not have acceptable tack ratings. Therefore it is possible that the reason satisfactory creams cannot be prepared using high surface area PTFE resins is because high solids creams cannot be prepared from them. Comparing the protective and tack results obtained with creams prepared using relatively monodisperse oils such as Galden D40 and Fomblin Y25 with those obtained using blended oils of similar viscosities such as Krytox GPL102 and 104 suggests it is probably preferable to utilize relatively monodisperse oils in preparing the creams of the invention. The Krytox oils are blends of a very low viscosity (about 7 cSt) oil and a high viscosity (about 1500 cSt) oil. Therefore it is preferred to utilize compositions based on relatively monodisperse base oils which do not contain very low viscosity oils and/or high viscosity oils.

I claim:

1. A topical skin protectant composition which comprises a dispersion of from at least 35% to about 50% by weight of finely divided polytetrafluoroethylene having a surface area below about 6 M$^2$/g in a liquid perfluorinated polyether having a viscosity between about 20 cSt and about 350 cSt.

2. The composition of claim 1 wherein at least 90% of the finely divided polytetrafluoroethylene has a particle size below about 5μ.

3. The composition of claim 1 wherein the perfluorinated polyether is based on perfluoropropylene oxide.

4. The composition of claim 1 wherein the polytetrafluoroethylene has a surface area below about 4 M$^2$/g.

5. The composition of claim 1 wherein the polytetrafluoroethylene has a surface area below about 4 M$^2$/g and at least 90% has a particle size below about 5μ.

6. A topical skin protectant composition which comprises a dispersion of from at least 35% to about 50% by weight of finely divided polytetrafluoroethylene having a surface area below about 6 M$^2$/g in a liquid perfluorinated polyether having a viscosity between about 20 cSt and about 350 cSt.

7. The composition of claim 6 wherein at least 90% of the finely divided polytetrafluoroethylene has a particle size below about 5μ.

8. The composition of claim 6 wherein the perfluorinated polyether is based on perfluoropropylene oxide.

9. The composition of claim 6 wherein the polytetrafluoroethylene has a surface area below about 4 M$^2$/g.

10. The composition of claim 6 wherein the polytetrafluoroethylene has a surface area below about 4 M$^2$/g and at least 90% has a particle size below about 5μ.

11. A process for preparing a topical skin protectant composition which comprises subjecting a mixture of from at least 35% to about 50% by weight finely divided polytetrafluoroethylene having a surface area below about 6 M$^2$/g in a perfluorinated polyether having a viscosity between about 20 cSt and about 350 cSt to high shear mixing.

* * * * *